United States Patent
Spiluttini Hebert

(10) Patent No.: US 11,051,752 B2
(45) Date of Patent: Jul. 6, 2021

(54) SYSTEM AND METHOD FOR CHARACTERIZING THE SLEEP OF AN INDIVIDUAL

(71) Applicant: URGOTECH, Paris (FR)

(72) Inventor: Béatrice Spiluttini Hebert, Houilles (FR)

(73) Assignee: URGOTECH, Paris (FR)

( * ) Notice: Subject to any disclaimer, the term of this patent is extended or adjusted under 35 U.S.C. 154(b) by 594 days.

(21) Appl. No.: 15/738,316

(22) PCT Filed: Jul. 7, 2016

(86) PCT No.: PCT/FR2016/051730
§ 371 (c)(1),
(2) Date: Jun. 1, 2018

(87) PCT Pub. No.: WO2017/006062
PCT Pub. Date: Jan. 12, 2017

(65) Prior Publication Data
US 2018/0263553 A1  Sep. 20, 2018

(30) Foreign Application Priority Data

Jul. 7, 2015  (FR) ...................... 1556421

(51) Int. Cl.
| | | |
|---|---|---|
| A61B 5/00 | (2006.01) | |
| A61B 5/374 | (2021.01) | |
| A61M 21/02 | (2006.01) | |
| A61B 5/316 | (2021.01) | |

(Continued)

(52) U.S. Cl.
CPC ............ *A61B 5/4815* (2013.01); *A61B 5/316* (2021.01); *A61B 5/374* (2021.01); *A61B 5/375* (2021.01);

(Continued)

(58) Field of Classification Search
CPC combination set(s) only.
See application file for complete search history.

(56) References Cited

U.S. PATENT DOCUMENTS 5,267,570 A    12/1993  Preston
2006/0293608 A1*  12/2006  Rothman ............. A61B 5/4812
                                                              600/545

(Continued)

FOREIGN PATENT DOCUMENTS

KR     20140128018    11/2014
WO     2009126179     10/2009

(Continued)

OTHER PUBLICATIONS

Werth et al. Spindle frequency activity in the sleep EEG: individual differences and topographic distribution. Electroencephalography and clinical Neurophysiology 103 (1997) 535-542. (Year: 1997).*

(Continued)

*Primary Examiner* — Etsub D Berhanu
(74) *Attorney, Agent, or Firm* — McAndrews, Held & Malloy, Ltd.

(57) ABSTRACT

The invention relates to a system for characterising the sleep of an individual, the characterisation system comprising: a measuring device for measuring a brain activity signal representing the brain waves; a central electronic unit for identifying, in a range of frequencies of between 9 and 16 Hz, a smaller range of sleep spindles of the individual, the smaller range of sleep spindles comprising the brain wave frequencies of the sleeping individual, having an amplitude higher than 15 μV and a duration of between 0.5 seconds and 2 seconds, and comparing, with a threshold, at least one parameter of the brain activity signal of the awake individual in the range of frequencies corresponding to the smaller range of sleep spindles; and a communication interface connected to the central unit and used to emit a warning (Continued)

Figure 1:
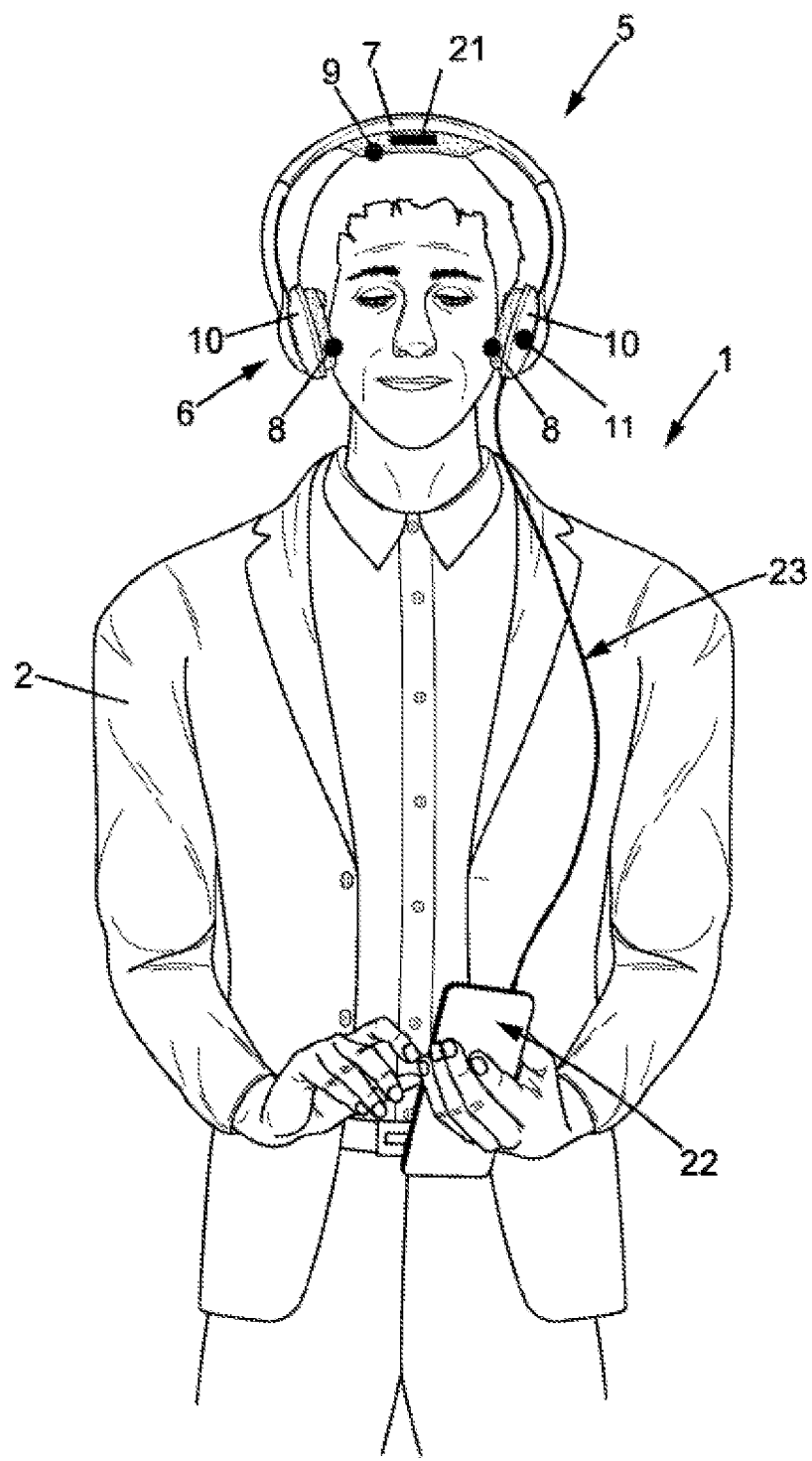

signal perceptible by the individual when the parameter of the brain activity signal in the range of frequencies corresponding to the smaller range of sleep spindles exceeds the threshold.

17 Claims, 3 Drawing Sheets

(51) Int. Cl.
    *A61B 5/375*     (2021.01)
    *A61M 21/00*     (2006.01)
    *A61B 5/291*     (2021.01)

(52) U.S. Cl.
    CPC .......... *A61B 5/4806* (2013.01); *A61B 5/4809* (2013.01); *A61M 21/02* (2013.01); *A61B 5/291* (2021.01); *A61B 5/4812* (2013.01); *A61B 5/4836* (2013.01); *A61M 2021/0011* (2013.01); *A61M 2230/10* (2013.01)

(56) References Cited

U.S. PATENT DOCUMENTS

| | | |
|---|---|---|
| 2013/0150659 A1 | 6/2013 | Shaw et al. |
| 2013/0267866 A1* | 10/2013 | Nakashima .......... A61B 5/0476 600/544 |
| 2014/0316230 A1 | 10/2014 | Denison et al. |

FOREIGN PATENT DOCUMENTS

| | | | |
|---|---|---|---|
| WO | 2014175684 | 10/2014 | |
| WO | WO-2014170781 A1 * | 10/2014 | .......... A61B 5/4812 |

OTHER PUBLICATIONS

Gennaro et al. An electroencephalographic fingerprint of human sleep. NeuroImage 26 (2005) 114-122. (Year: 2005).*

Huupponen et al., "Automatic analysis of electro-encephalogram sleep spindle frequency throughout the night", Med. Biol. Eng. Comput., 2003, 41, 727-732.

Schabus et al., "Interindividual sleep spindle differences and their relation to learning-related enhancements", Brain Research 1191 (2008) 127-135.

Fogel et al., "The function of the sleep spindle: A physiological index of intelligence and a mechanism for sleep-dependent memory consolidation", Neuroscience and Biobehavioral Reviews 35 (2011) 1154-1165.

Kabir et al., "Enhanced automated sleep spindle detection algorithm based on synchrosqueezing", Med Biol Eng Comput (2015) 53: 635-644.

* cited by examiner

SYSTEM AND METHOD FOR CHARACTERIZING THE SLEEP OF AN INDIVIDUAL

The invention relates to a system and a method for characterization of sleep of an individual.

In particular, the invention is applied to increasing the density (i.e. the number over a defined period) and/or the amplitude of the sleep spindles.

Furthermore, the present invention is intended not only for persons who are subject to sleep disorders such as insomnia, but more generally for anyone wishing to improve their recuperation capacity, in particular during or following an effort, a journey, a situation of stress etc.

Sleep spindles are brain activity electrical signals with frequencies generally comprised between 9 and 16 Hz (Molle et al., 2011) and an amplitude from 25 to 150 microvolts. Low frequency and high frequency sleep spindles are found, which are variable and specific to each individual. The sleep spindles generally last between 0.5 and 2 seconds and are the product of an activity of the reticulo-thalamo-cortical system.

Sleep spindles, as their name indicates, appear during sleep, and more particularly during the light sleep phase (phase called stage N2 of NREM—for non-rapid eye movement-sleep) (De Gennaro & Ferrara, 2003; De Gennaro, Ferrara, Curcio, & Cristiani, 2001). In fact, it is noteworthy that they appear in larger numbers during this phase. They are also found in deep sleep (phase called sleep stage N3) but prove to be rarer or even absent in so-called paradoxal sleep (phase called sleep stage N4 or REM sleep). Sleep spindles are often called "sleep guardians" and a high density of sleep spindles is generally associated with effective sleep. Conversely, the scientific literature has recently shown that a low density of sleep spindles seems to be the sign of sleep disturbed by stress (Dang-Vu et al., 2015).

At present, it has been demonstrated that certain medicinal products of the class of hypnotic medicinal products lead to an increase in the density of sleep spindles. Nevertheless, this type of medication appears to be intended only for patients having defined symptomatology. Furthermore, these drugs have side effects and can lead to a certain dependency.

Other techniques aiming at improving the generation of sleep spindles should be envisaged.

Thus, novel techniques have been developed making it possible to lead an individual to act on a biological activity by means of a feedback treatment also called biofeedback. In the particular case of action on a nervous or neurological activity, the neurofeedback treatment consists, for example, in training the individual to help them to relax, and encourage them to modify their brain activity, in particular by the production of a certain class of brain waves.

On the basis of a first study carried out on cats (Sterman, Howe, & Macdonald, 1970) successive researches have demonstrated that applying the neurofeedback treatment could lead to improving the time taken to fall asleep and the quality of sleep of an individual. This neurofeedback treatment device is aimed at encouraging the production of μ or sensorimotor rhythm (SMR) waves. The frequency of these waves is generally comprised between 9 Hz and 16 Hz. These waves appear on falling asleep (phase called sleep stage N1), i.e. the transition between wakefulness and sleep. This phase is often accompanied by signs of fatigue such as yawning. This phase is where SMR and α waves occur. The α waves have a frequency generally comprised between 8 Hz and 13 Hz and are generally associated with attention and vigilance. The SMR waves can also be present in a state of relaxation in the awake state. They then disappear in a state of attentiveness. Given that the alpha and SMR waves can have overlapping frequencies or that certain filters can allow part of the brain activity corresponding to the frequency window of the alpha waves to pass through, the specific training of SMR waves can be compromised to the extent that it is the alpha waves that will be trained and not the SMR waves.

In parallel, the training of SMR waves is also used in different applications such as those aiming at improving the symptoms of attention deficit disorders with or without hyperactivity (Ams, Feddema, & Kenemans, 2014), relaxation and, as described in document US 2013/150659, improving sleep (see also Cortoos et al., 2010). The training of SMR waves would allow an improvement in certain cognitive performances (Schabus et al., Brain Research (2008), 1191, 127-135 and Stuart et al., Neuroscience and Biobehaviour (2011), 35, 1154-1165) and motor performances. However, certain disparities exist in the effectiveness of such a neurofeedback treatment depending on the individuals, in particular in the fact that, thus far, the teaching from the prior art has always relied on the absence of taking into account a personalization or a specific adaptation of such a treatment to a particular individual.

The invention thus aims at overcoming the problems mentioned above.

The inventors have thus discovered that the sleep spindles, which have a frequency specific to each individual, play a significant role during the light sleep phase due to their inhibiting effect on awakening. They have, moreover, discovered that training the brain waves in the awake state, in the specific range corresponding to the sleep spindles of the individual, leads to an improvement in the amplitude and the density of the sleep spindles in the asleep state thus contributing to improving the quality of sleep. Conversely, according to different methods that are known and disclosed in the prior art such as those described in document US 2013/150659, a training of the brain waves emitted by the individual in the awake state and based on frequency intervals of standardized SMR waves without taking into account any range of specific frequencies corresponding to the sleep spindles emitted specifically by an individual in the asleep state, does not allow effective personalization of a treatment to a particular individual. Such a treatment only allows the stimulation of certain SMR waves, the frequencies of which do not necessarily correspond to those of the sleep spindles of said individual in the asleep state. This type of training, which does not make it possible to guarantee or at least to simply and rapidly obtain an increase in the density and amplitude of the sleep spindles, does not offer satisfactory effectiveness on the treatment of sleep disorders in particular.

To this end, the invention proposes a system for characterization of sleep of an individual, comprising:
  a measuring device adapted to measure a brain activity signal representative of the brain waves.
  an electronic central unit adapted to:
  identify, in a range of frequencies from 9 to 16 Hz, at least one reduced range of sleep spindles specific to the individual, the reduced range of sleep spindles comprising frequencies of the brain waves of the sleeping individual having an amplitude greater than 15 μV and a duration comprised between 0.5 second and 2 seconds,
  compare at least one parameter of the brain activity signal of the awake individual in the range of frequencies corresponding to the reduced range of sleep spindles, to a threshold, a communication interface linked to the central unit and adapted to emit a warning signal perceptible to the individual when the parameter of the brain activity signal in the range of frequencies corresponding to the reduced range of sleep spindles exceeds the threshold, preferentially during a defined period of time, such as at least 0.25 seconds.

It is important to note that, in addition to characterizing the density and/or the amplitude of the sleep spindles specific to the individual, the system forming the subject-matter of the present invention can also make it possible to characterize the individual frequency of an alpha peak (iAPF) in the two first minutes during which the individual's eyes are closed. This characterization then provides information about the best choices of filtering parameters to be put in place in order to select at least one reduced range of the sleep spindles and/or to modify parameters of frequencies, for example by installing higher order and more specific filters. This selection makes it possible to avoid any overlapping between the specific frequency band to be trained, corresponding to the sleep spindles, and the specific frequency band of the alpha waves that it is not desired to train. These arrangements make it possible to better characterize the reduced range of sleep spindles specific to the individual and thus to improve the training. The user can thus more effectively improve the quality of their sleep.

The frequency of alpha waves is generally comprised between 7 and 13 Hz. The power spectral density of the alpha waves corresponds to the distribution of the amplitude in volts of these waves between the frequencies ranging from 7 to 13 Hz. In order to obtain the signal of the alpha waves, the power spectrum between 7 and 13 Hz, i.e. the amplitude of these waves obtained in the subject in the awake state, having eyes open, is subtracted from the spectrum of the same individual in the awake state having eyes closed. This therefore amounts to retaining only the overall power spectrum of the alpha waves which therefore defines the individual frequency of the alpha peak of a particular individual. The individual frequency of the alpha peak thus corresponds to the absolute maximum of the amplitude in this window of frequencies ranging from 7 to 13 Hz. (Klimesch W. EEG-alpha rhythms and memory processes. Int J Psychophysiol 1997; 26: 319-40). The individual frequency on the alpha peak can be measured (in Hertz) according to another embodiment, by means of the following calculation: a ratio of the weighted sum of spectral powers in a window of frequencies comprised between 7 and 13 Hz to the total spectral power of the alpha waves in the window, the spectral waves of the weighted sum being weighted by the frequencies of the window:

$$\left(\sum_{i=7}^{13} (a_i(f_i) \times f_i)\right) / \sum_{i=7}^{13} a_i(f_i)$$

with $f_i$ the frequency i of the alpha waves, and
$a_i(f_i)$, the amplitude of the alpha waves at the frequency i.

Once the individual frequency of the alpha peak has been defined specifically for a particular individual, it then makes it possible to characterize a tangible boundary between the frequencies of the alpha waves and those of the sleep spindles of the individual in question, and therefore to be free from all of the alpha waves having a frequency close to that of the sleep spindles in order to allow an analysis of the frequencies of the sleep spindles not polluted by the frequencies of the alpha waves.

Thus, according to another embodiment, the system for characterization comprises an electronic central unit which is adapted to identify, prior to the sleep spindles and within a window of frequencies comprised between 7 and 13 Hz, the individual frequency of the alpha peak of the individual.

The latter is therefore defined within a window of frequencies comprised between 7 and 13 Hz and after subtraction of the power spectrum obtained in an individual having eyes open from that obtained in an individual having eyes closed.

Furthermore, the question of the specificity of the training can also be improved by measuring this individual frequency of the alpha waves with the aim of providing more specific feedback at the level of the generation of the sleep spindles, while preventing an unwanted alpha signal from interfering with the latter.

The system for characterization implements, during first use or with each new use, a phase of learning to specifically characterize the sleep of the individual by identifying the sleep spindles which are specific to them and to allow the training of said sleep spindles. By thus distinguishing for each individual the range of frequencies to be trained, the effectiveness of the neurofeedback treatment on a set of individuals can be improved.

In order to identify the reduced range(s) of sleep spindles, the electronic central unit can be adapted to detect, in the range of frequencies from 9 to 16 Hz of the brain activity signal of the sleeping individual, the brain waves of the sleeping individual having an amplitude greater than 15 µV and a duration comprised between 0.5 second and 2 seconds, Alternatively, in order to identify the reduced range of sleep spindles, the electronic central unit can be adapted to:
  determine, in the range of frequencies from 9 to 16 Hz of the brain activity signal of the sleeping individual, a plurality of reduced ranges of frequencies,
  compare the parameter of the brain activity signal of the sleeping individual in each of the reduced ranges of frequencies to the threshold,
  define the reduced range of sleep spindles as the reduced range of frequencies in which the brain activity signal exceeds the threshold a greater number of times.

The measuring device can comprise:
  a support intended to be placed on the head of the individual, and
  at least one ground electrode, one reference electrode and one measuring electrode, which can optionally be combined within the same electrode having both functions, more particularly the reference and measuring functions, connected to the central unit and arranged on the support for measuring a difference in electric potential between the reference, ground and measuring electrodes as brain activity signal.

The central unit can be mounted on the support and be adapted to amplify the brain activity signal.

The central unit can be adapted to digitize the brain activity signal.

The reference electrodes, but also the ground and measuring electrodes can be dry electrodes. They can, however, also be wet electrodes, semi-dry electrodes or also semi-wet electrodes. According to a particular embodiment of the invention, each type of electrode can have a particular and different nature.

The communication interface can be carried manually by the individual.

The central unit can be located within a headset linked to the communication interface or also within an external or remote device, such as a server.

The central unit can be adapted to modify, i.e. raise or lower the threshold and/or a period of time above the threshold.

The parameter of the brain activity signal can be selected among an amplitude and a density.

According to a second aspect, the invention proposes a method for characterization of sleep of an individual, comprising the steps consisting in:
  measuring a brain activity signal representative of brain waves.
  identifying, in a range of frequencies from 9 to 16 Hz, at least one reduced range of sleep spindles specific to the individual, the reduced range of sleep spindles comprising frequencies of brain waves of the sleeping individual having an amplitude greater than 15 µV and a duration comprised between 0.5 second and 2 seconds,
  comparing at least one parameter of the brain activity signal of the awake individual in the range of frequencies corresponding to the reduced range of sleep spindles, to a threshold and emitting a warning signal perceptible to the individual when the parameter of the brain activity signal in the range or ranges of frequencies corresponding to the reduced range or ranges of sleep spindles exceeds the threshold.

The step consisting in identifying the reduced range of sleep spindles can comprise detecting, in the range of frequencies from 9 to 16 Hz of the brain activity signal of the sleeping individual, brain waves of the sleeping individual having an amplitude greater than 15 µV and a duration comprised between 0.5 second and 2 seconds, Alternatively, the step consisting in identifying the reduced range of sleep spindles can comprise:
  determining, in the range of frequencies from 9 to 16 Hz of the brain activity signal of the sleeping individual, a plurality of reduced ranges of frequencies,
  comparing the parameter of the brain activity signal of the sleeping individual in each of the reduced ranges of frequencies to the threshold,
  defining the reduced range of sleep spindles as the reduced range of frequencies in which the parameter of the brain activity signal exceeds the threshold a greater number of times.

According to another embodiment, the method for characterization can comprise, during the step consisting in identifying the reduced range of sleep spindles, a prior identification of the individual frequency of the alpha peak of the individual, defined within a window of frequencies comprised between 7 and 13 Hz. The power spectral density of the alpha waves corresponds to the distribution of the amplitude in volts of these waves between the frequencies ranging from 7 to 13 Hz. In order to obtain the signal of the alpha waves, the power spectrum between 7 and 13 Hz, i.e. the amplitude of these waves obtained in the subject in the awake state having eyes open, is subtracted from the spectrum of the same individual in the awake state having eyes closed. The individual frequency of the alpha peak thus corresponds to the absolute maximum of the amplitude in this window of frequencies ranging from 7 to 13 Hz. (Klimesch W. EEG-alpha rhythms and memory processes. Int J Psychophysiol 1997; 26: 319-40). The individual frequency of the alpha peak can be measured (in Hertz) according to another embodiment, by means of the following calculation: a ratio of the weighted sum of spectral powers in a window of frequencies comprised between 7 and 13 Hz to the total spectral power of the alpha waves in the window, the spectral powers of the weighted sum being weighted by the frequencies of the window:

$$\left(\sum_{i=7}^{13} (a_i(f_i) \times f_i)\right) / \sum_{i=7}^{13} a_i(f_i)$$

with $f_i$ the frequency i of the alpha waves, and
$a_i(f_i)$, the amplitude of the alpha waves at the frequency i.

Once the individual frequency of the alpha peak has been defined specifically for a particular individual, it then makes it possible to characterize one or more tangible boundaries making it possible to discriminate between the frequencies of the alpha waves and those of the sleep spindles of the individual in question, and therefore to be free from all of the alpha waves having a frequency close to that of the sleep spindles in order to allow an analysis of the frequencies of the sleep spindles not polluted by the frequencies of the alpha waves.

The step consisting in measuring the brain activity signal can comprise a measurement of a difference in electric potential between reference, ground and measuring electrodes.

The method for characterization can provide:
  prior to the step consisting in comparing the parameter of the brain activity signal to the threshold, amplifying the brain activity signal and
  during the step consisting in comparing the parameter of the brain activity signal to the threshold, comparing the parameter of the amplified brain activity signal to the threshold.

The method for characterization can provide:
  prior to the step consisting in comparing the parameter of the brain activity signal to the threshold, digitizing the brain activity signal and
  during the step consisting in comparing the parameter of the brain activity signal to the threshold, comparing the digitized brain activity signal to the threshold.

The method for characterization can provide, during the step consisting in comparing the parameter of the brain activity signal to the threshold, modifying the threshold. By "modifying the threshold", is meant any action aiming at raising or lowering the level of the threshold.

The method for characterization can provide, during the step consisting in comparing the parameter of the brain activity signal to the threshold, selecting the parameter among an amplitude and a density.

Figure 2:
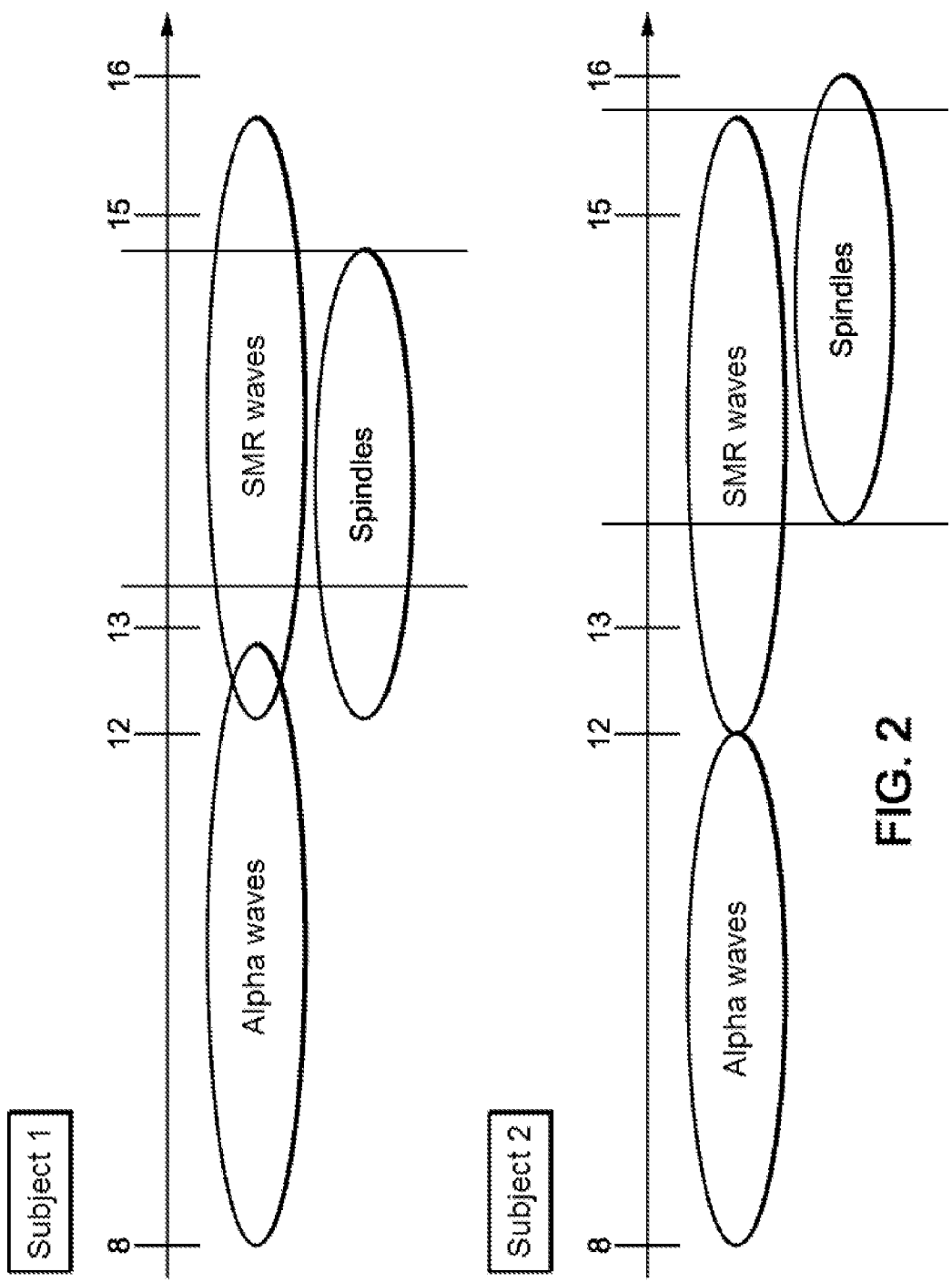
Figure 3:

Further aims and advantages of the invention will become apparent on reading the following description of a particular embodiment of the invention, given by way of non-limitative example, the description being given with reference to the attached drawings in which:

FIG. 1 is a representation of a system for characterization of sleep of an individual, comprising a measuring device in the form of a headset adapted to measure a brain activity signal representative of brain waves, and an electronic central unit adapted to identify at least one reduced range of sleep spindles specific to the individual, and a manually portable communication interface intended to emit a warning signal when a parameter of the brain signal activity in the reduced range of sleep spindles exceeds a threshold, FIG. 2 is a schematic representation of the ranges of frequencies of α and µ or Sensori-Motor Rhythm (SMR) waves emitted in the phase of drowsiness, and sleep spindles emitted in the phase of light sleep by two different individuals, FIG. 3 is a representation of the brain activity signal representative of the brain waves of the individual acquired by the measuring device of FIG. 1, identifying the reduced range of sleep spindles specific to the individual.

Figure 4:
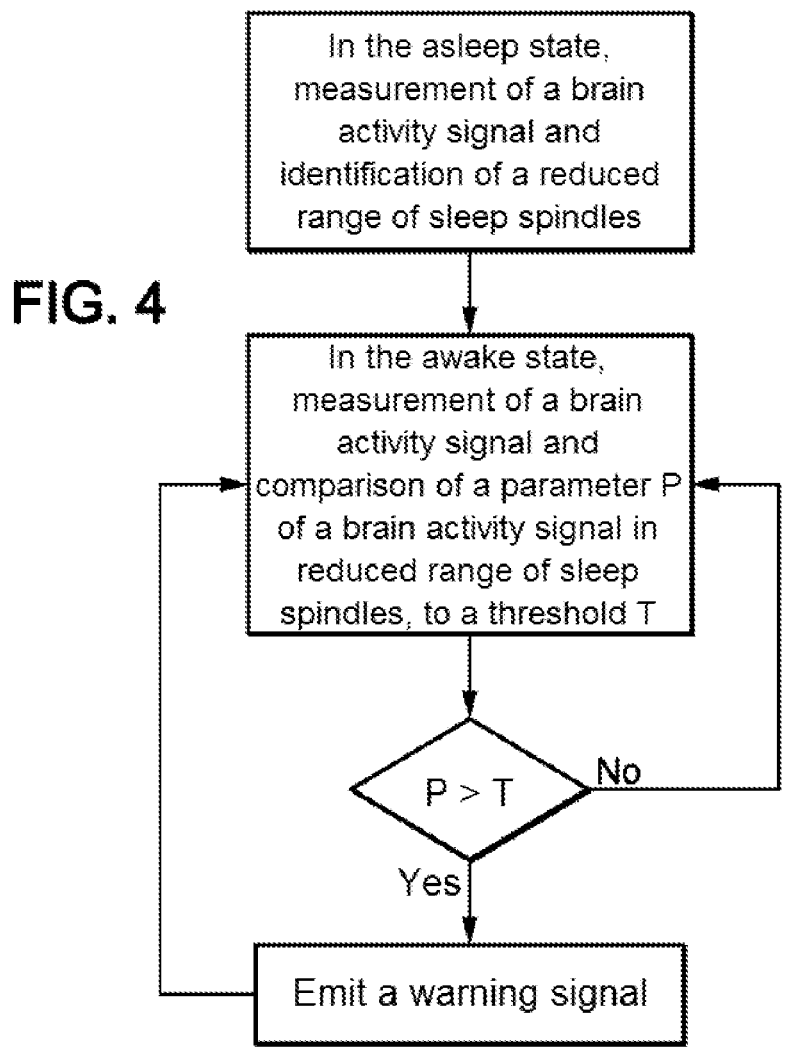

FIG. 4 is a diagram illustrating a method for the characterization of sleep, implemented by the system for characterization of sleep of FIG. 1.

In the figures, the same reference numbers denote identical or similar elements.

FIG. 1 shows an embodiment of a system for characterization 1 of sleep of a user 2 intended to be used in a neurofeedback treatment in order to improve the speed of falling asleep and the quality of sleep of the user 2.

The system for characterization 1 comprises:
- a measuring device 5 adapted to measure a brain activity signal representative of the brain waves of the brain of the user 2, and
- an electronic central unit 21 for processing the brain activity signal,
- a communication interface 22 with the user 2.

The measuring device 5 is in the form of a headset 6 comprising a support 7, optionally adjustable, intended to be placed on the head of the user 2. The brain activity signal is measured in the form of a difference in electric potential between one or more reference electrodes 8, a ground electrode 11 and one or more measuring electrodes 9 suitably arranged on the support 7. The reference 8, measuring 9 and ground 11 electrodes are, preferably, dry electrodes.

The reference 8, ground 11 and measuring 9 electrodes and the electronic processor are connected by a wired 23 or wireless connection to the central unit 21. The central unit 21 can comprise an electronic processor, an amplifier adapted to amplify the brain activity signal and an analogue-to-digital converter suitable for digitizing the brain activity signal. The brain activity signal acquired by the reference 8, ground 11 and measuring 9 electrodes, then digitized and amplified can thus be transmitted to the processor of the central unit 21 for processing. Without being limited thereto, the central unit 21 can be provided in the headset 6.

The central unit 21 is linked to the communication interface 22 with the user. In the embodiment shown, the communication interface 22 comprises two headphones 10 mounted on the headset 6 to be able to be placed over the ears of the user 2 in order to be able to deliver an audible warning signal representative of the emission of a particular brainwave. The communication interface 22 also comprises any other appropriate manually portable electronic device, such as a mobile phone, a tablet, a PDA or other device. The communication interface 22 can in particular comprise a screen for displaying a warning signal, in particular visual. The screen can be a touch screen for interacting with the central unit 21. Additionally or alternatively, an interaction with the central unit 21 can be obtained via a keyboard, one or more activation buttons, a memory card reader or other device belonging to the communication interface 22.

FIG. 2 illustrates the frequency decomposition of the brain activity signal of two individuals.

In a phase of drowsiness and falling asleep, the brain activity of each of the individuals, then in an awake state, is characterized by:
- α waves emitted in a range of frequencies comprised between 8 Hz and 13 Hz for one of the individuals identified as subject 1, and in a range of frequencies comprised between 8 Hz and 12 Hz for the other individual identified as subject 2,
- μ or Sensori-Motor Rhythm (SMR) waves emitted in a range of frequencies comprised between 12 Hz and 15.5 Hz for subject 1 and subject 2.

In a phase of light sleep, the brain activity of each of the individuals, then in an asleep state, is characterized by sleep spindles emitted in a reduced range of sleep spindles comprised between 12 Hz and 15 Hz for subject 1, and in a reduced range of sleep spindles comprised between 13.5 Hz and 16 Hz for subject 2. It is clear that the reduced range of sleep spindles, the inhibiting effect on awakening of which plays a significant role during the light sleep phase, is specific to each individual.

In order to characterize the sleep of the user 2, the central unit 21 is adapted to carry out a frequency decomposition of the brain activity signal and to identify, in a range of frequencies from 9 to 16, the reduced range(s) of sleep spindles specific to the user 2. In particular, the reduced range(s) of sleep spindles comprise the frequencies of brain waves of the user 2 in the asleep state having an amplitude greater than 15 µV and a duration comprised between 0.5 second and 2 seconds, As shown in FIG. 3 which illustrates a brain activity signal acquired during the light sleep phase of the user 2, the identification of a reduced range of sleep spindles can be carried out in the asleep state of the user 2 by detecting, in the range of frequencies from 9 to 16 Hz of the brain activity signal during the light sleep phase, brain waves having an amplitude greater than 15 µV and a duration comprised between 0.5 second and 2 seconds, Alternatively, the identification of the reduced range of sleep spindles could be carried out by an iterative process consisting in modulating a reduced range of frequencies until the reduced range of frequencies corresponding to that of the sleep spindles is identified. In particular, the iterative process involves determining, in the range of frequencies from 9 to 16 Hz of the brain activity signal of the sleeping individual, a plurality of reduced ranges of frequencies. In each of the reduced ranges of frequencies, a parameter, such as an amplitude or a density, i.e. a number of peaks exhibiting a minimal amplitude over a defined period, of the brain activity signal of the sleeping individual, is compared to a threshold representative of the same parameter for the sleep spindles. The reduced range of sleep spindles can then be defined as the reduced range of frequencies in which the brain activity signal exceeds the threshold a greater number of times.

In the awake state of the user 2, the central unit 21 can then compare at least one parameter of the brain activity signal in the awake state in the range of frequencies corresponding to the reduced range of sleep spindles to a threshold. The range of frequencies corresponding to the reduced range of sleep spindles is different, generally being narrower than and possibly offset from the range of frequencies of the SMR waves. The parameter is, for example, selected among an amplitude and a density, i.e. a number of peaks exhibiting a defined minimal amplitude over a defined period.

The central unit 21 is then adapted to control the emission of the audible warning signal in the headphones 10 and of the visual warning signal on the screen of the communication interface 22 when the parameter of the brain activity signal in the range of frequencies corresponding to the reduced range of sleep spindles exceeds the threshold, preferentially during a defined period of time, such as at least 0.25 seconds.

With reference to FIG. 4, a method for the characterization of the sleep of the user, implemented with the system for characterization of sleep is now described.

In the asleep state, the difference in electric potential between the reference 8, ground 11 and measuring electrodes 9 is measured by the headset 6 in order to obtain the brain activity signal representative of the brain waves of the user 2. This brain activity signal is amplified and digitized by the central unit 21.

In the range of frequencies from 9 to 16 Hz of the brain activity signal in the light sleep phase, the central unit 21 identifies the reduced range of sleep spindles of the user 2, This reduced range of sleep spindles comprises the frequencies of brain waves of the sleeping user having an amplitude greater than 15 µV and a duration comprised between 0.5 second and 2 seconds, In the awake state, the difference in electric potential between the reference 8, ground 11 and measuring 9 electrodes is measured by the headset 6 in order to obtain the brain activity signal representative of the brain waves of the user 2. This brain activity signal is amplified and digitized by the central unit 21.

In the range of frequencies corresponding to the reduced range of sleep spindles, the central unit 21 compares at least one of the following two parameters, which are the amplitude or the density, to the threshold.

When the parameter of the brain activity signal in the range of frequencies corresponding to the reduced range of sleep spindles exceeds the threshold, if appropriate beyond a defined period of time, the audible warning signal is emitted in the headphones 10 and the visual warning signal is displayed via the communication interface 22. Additionally or alternatively, the communication interface 22 can be adapted to emit any other type of warning signal and in particular, tactile, olfactory or also gustatory.

The user 2 is thus warned of the emission of brain waves promoting the quality of sleep.

On the basis of this characterization of the sleep, a neurofeedback treatment can be put in place to improve the quality of the sleep of the user 2. The neurofeedback treatment then comprises training aiming at encouraging the user 2 to produce the desired brain waves. The training comprises one or more sequences of relaxation and exercises rewarding the emission of the desired brain waves by particular warning signals.

During the training, the threshold can be increased to cause the user 2 to progress in the production of appropriate brain waves. During the training, the threshold can also be lowered to facilitate the task of a user performing less well. Additionally or alternatively, it is possible to change the defined period during which the threshold must be exceeded in order to emit the warning signal, in order to make the training more complex or simpler.

The invention claimed is:

1. A system for characterization of sleep of an individual, the system for characterization comprising:
a measuring device adapted to measure a brain activity signal representative of brain waves of the individual, the measuring device comprising a support intended to be placed on the head of the individual, and at least one reference electrode, one ground electrode and one measuring electrode arranged on the support for measuring a difference in electric potential between the reference, ground and measuring electrodes as the brain activity signal,
an electronic central unit connected to said at least one reference electrode, one ground electrode and one measuring electrode, and adapted to:
identify, in a range of frequencies from 9 to 16 Hz, at least one reduced range of sleep spindles specific to the individual, the reduced range of sleep spindles comprising frequencies of a sleeping brain activity signal of the individual in a sleeping state having an amplitude greater than 15 µV and a duration comprised between 0.5 second and 2 seconds,
compare a parameter of an awake brain activity signal of the individual in an awake state in the range of frequencies corresponding to the reduced range of sleep spindles, to a threshold, the parameter being selected from among an amplitude of the awake brain activity signal and a density of the awake brain activity signal, the density being a number of peaks exhibiting a minimal amplitude over a defined period, and
a communication interface linked to the central unit and adapted to emit a warning signal perceptible to the individual when the parameter exceeds the threshold.

2. The system for characterization according to claim 1, wherein, in order to identify the reduced range of sleep spindles, the electronic central unit is adapted to identify a ratio representative of an alpha peak of the individual, the ratio being that of a weighted sum of spectral powers in a window of frequencies comprised between 7 and 13 Hz, to a total spectral power of alpha waves in the window, the spectral powers of the weighted sum being weighted by the frequencies of the window:

$$\left(\sum_{i=7}^{13}(a_i(f_i) \times f_i)\right) / \sum_{i=7}^{13} a_i(f_i)$$

with $f_i$ the frequency i of the alpha waves, and $a_i(f_i)$, the amplitude of the alpha waves at the frequency i.

3. The system for characterization according to claim 1, wherein the central unit is mounted on the support and is adapted to amplify the measured brain activity signal.

4. The system for characterization according to claim 3, wherein the central unit is adapted to digitize the brain activity signal.

5. The system for characterization according to claim 1, wherein the reference, ground and measuring electrodes are dry electrodes.

6. The system for characterization according to claim 1, wherein the communication interface is manually portable by the individual.

7. The system for characterization according to claim 1, wherein the central unit is adapted to compare the parameter to the threshold for several iterations, and to modify the threshold between at least two iterations.

8. The system for characterization according to claim 1, wherein the communication interface is adapted to emit the warning signal when the parameter exceeds the threshold for a period of time.

9. The system for characterization according to claim 8, wherein the central unit is adapted to compare the parameter to the threshold for several iterations, and to modify the period of time between at least two iterations.

10. The method for characterization of sleep of an individual comprising the steps of:
measuring a brain activity signal representative of brain waves of the individual by placing a support of a measuring device on the head of the individual, the measuring device comprising at least one reference electrode, one ground electrode and one measuring electrode arranged on the support for measuring a difference in electric potential between the reference, ground and measuring electrodes as the brain activity signal, identifying, in a range of frequencies from 9 to 16 Hz, at least one reduced range of sleep spindles specific to the individual, the reduced range of sleep spindles comprising frequencies of a sleeping brain activity signal of the individual in a sleeping state having an amplitude greater than 15 µV and a duration comprised between 0.5 second and 2 seconds, comparing a parameter of an awake brain activity signal of the individual in an awake state in the range of frequencies corresponding to the reduced range of sleep spindles, to a threshold, and emitting a warning signal perceptible to the individual when the parameter exceeds the threshold.

11. The method for characterization according to claim 10, wherein the step of identifying the reduced range of sleep spindles comprises an identification of a ratio representative of an alpha peak of the individual, the ratio being that of a weighted sum of spectral powers in a window of frequencies comprised between 7 and 13 Hz, to a total spectral power of the alpha waves in the window, the spectral powers of the weighted sum being weighted by the frequencies of the window:

$$\left(\sum_{i=7}^{13} (a_i(f_i) \times f_i)\right) / \sum_{i=7}^{13} a_i(f_i)$$

with $f_i$ the frequency i of the alpha waves, and $a_i(f_i)$, the amplitude of the alpha waves at the frequency i.

12. The method for characterization according to claim 10, further comprising:

prior to the step consisting inof comparing the parameter of the awake brain activity signal to the threshold, amplification of the measured brain activity signal and during the step of comparing the parameter of the awake brain activity signal to the threshold, comparison of the amplified brain activity signal to the threshold.

13. The method for characterization according to claim 10, further comprising:

prior to the step of comparing the parameter of the awake brain activity signal to the threshold, digitization of the measured brain activity signal and during the step of comparing the parameter of the awake brain activity signal to the threshold, comparison of the digitized brain activity signal to the threshold.

14. The method for characterization according to claim 10, wherein the step of comparing the parameter to the threshold is performed for several iterations, and wherein the threshold is modified between at least two iterations.

15. The method for characterization according to claim 10, further comprising, during the step of comparing the parameter of the awake brain activity signal to the threshold, selection of the parameter among an amplitude of the awake brain activity signal and a density of the awake brain activity signal, the density being a number of peaks exhibiting a minimal amplitude over a defined period.

16. The method for characterization according to claim 10, wherein the warning signal is emitted when the parameter exceeds the threshold for a period of time.

17. The method for characterization according to claim 16, wherein the step of comparing the parameter to the threshold is performed for several iterations, and wherein the period of time is modified between at least two iterations.

* * * * *